United States Patent [19]

Welch et al.

[11] Patent Number: 6,015,659
[45] Date of Patent: Jan. 18, 2000

[54] INDUCEMENT OF THERMOTOLERANCE WITH BENZOQUINONOID ANSAMYCINS

[75] Inventors: William J. Welch; Ramanujan Hegde, both of San Francisco, Calif.

[73] Assignee: The Regents of the University of California, Oakland, Calif.

[21] Appl. No.: 08/931,772

[22] Filed: Sep. 16, 1997

Related U.S. Application Data

[63] Continuation-in-part of application No. 08/432,842, May 2, 1995, abandoned.

[51] Int. Cl.$^7$ .............................. A01N 55/02; A01N 1/02
[52] U.S. Cl. ........................... 435/1.2; 435/1.1; 514/187; 540/461
[58] Field of Search ................................... 514/183, 244, 514/187; 435/1.1, 1.2, 2; 540/461

[56] References Cited

U.S. PATENT DOCUMENTS

| | | | |
|---|---|---|---|
| 4,261,989 | 4/1981 | Sasaki et al. | 424/244 |
| 5,914,345 | 6/1999 | Slepian et al. | 514/496 |

OTHER PUBLICATIONS

Carper, S.W., et al., Heat Shock Proteins in Thermotolerance and Other Cellular Processes (Oct. 1987) 47 Cancer Research, 5249–5255 (Previously submitted with the Information Disclosure Statement considered by the Patent Office on Jun. 15, 1996.
Fisher, G.A. et al., J. Cell Physiol., 128:127–132 (1986).
Haveman, J., et al., J. Radiat. Biol., 50:51–64 (1986).
Shibata, K., et al., J. Antibiot., 39:415–23 (1986).
Okabe, M., et al., Leuk. Res. 18:867–73 (1994).
Yoneda, T., et al., J. Clin. Invest. 91:2791–2795 (1993).
Villar, J., et al., Am. Rev. Respir. Dis., 147:177–181 (1993).
Perdizet, G.A., et al. Transplantation Proceedings, 25:1670–1673 (1993).
Brown, M.A., et al., Proc. Natl. Acad. Sci. USA, 89:3246–3250 (1992).
GIBO BRL *Herbimycin A Product Literature*.
S. Omura et al., "*Herbimycin, a New Antibiotic Produced by a Strain of Streptomyces*" (Apr. 1979) XXXII(4) *The Journal of Antibiotics*, 255–261.
Y. Murakami et al., "*Induction of HSP 72/73 by Herbimycin A, an Inhibitor of Transformation by Tyrosine Kinase Oncogenes*" (1991) 195 *Experimental Cell Research*, 338,344.
Y. Murakami et al., "*Reversal of Transformed Phenotypes by Herbimycin A in src Oncogene Expressed Rat Fibroblasts*" (Mar. 1988) 48 *Cancer Research*, 1587–1590.
S. Carper et al., "*Heat Shock Proteins in Thermotolerance and Other Cellular Processes*" (Oct. 19) 47 *Cancer Research*, 5249–5255.
W. Welch "*How Cells Respond to Stress*" (May 1993) 268(5) *Scientific American*, 55–64.
Y. Uehara et al., "*Irreversible Inhibition of VSCR SCR Tyrosine Kinase Activity by Herbimycin A and Its Abrogation by Sulfhydryl Compounds*" (Sep. 1989) 163(2) *Biochemical and Biophysical Research Communications*, 803–809.
K. Kondo et al., "Induction of In Vitro Differentiation of Mouse Embryonal Carcinoma (F9) and Erythroleukemia (MEL) Cells by Herbimycin A, an Inhibitor of Protein Phosphorylation" (Jul. 1989) 109 *The Journal of Cell Biology*, 285–293.
L. Whitesell et al., "Inhibition of Heat Shock Protein HSP90–pp60$^{v-src}$ Heteroprotein Complex Formation by Benzoquinone Ansamycins: Essential Role for Stress Proteins in Oncogenic Transformation" (Aug. 1944) 91, 8324–8328.

*Primary Examiner*—Sandra E. Saucier
*Attorney, Agent, or Firm*—Townsend and Townsend and Crew LLP

[57] ABSTRACT

Thermotolerant phenotypes are developed in cells, tissues, organs and organisms by the administration of benzoquinonoid ansamycins such as herbimycin A and any of various analogs. The general stress tolerance resulting from this inducement offers benefits in a variety of ways, including rendering surgical patients more able to withstand the rigors of surgery, prolonging the shelf life of organs excised from organ donors, and prolonging the viability of tissue-cultured cells and organs.

24 Claims, 1 Drawing Sheet

INDUCEMENT OF THERMOTOLERANCE WITH BENZOQUINONOID ANSAMYCINS

CROSS-REFERENCE TO RELATED APPLICATIONS

This application is a Continuation-in-Part of U.S. application Ser. No. 08/432,842, filed May 2, 1995 now abandoned.

GOVERNMENT RIGHTS

This invention was made at least in part with United States Government support under Grant Nos. GM 33551 and GM 07618 awarded by the National Institutes of Health, and Grant No. MCB 9018320 awarded by the National Science Foundation. The United States Government has certain rights in this invention.

FIELD OF THE INVENTION

This invention resides in the field of the heat stress response, and flirter relates to the administration and biological effects of certain benzoquinonoid ansamycin antibiotics.

BACKGROUND OF THE INVENTION

Heat shock or stress response is a phenomenon observed in living cells of all types that have been exposed at least temporarily to a temperature a few degrees above physiological growth temperature. One manifestation of this response is the appearance within the cells of abnormally folded proteins in general. Another manifestation is the increased expression of a family of proteins which under normal growth conditions are expressed by the same cells at lower levels. These proteins have therefore been termed "heat shock proteins" or, more recently, "stress proteins." The increased expression of the stress proteins and the accumulation of abnormally folded forms of other proteins have also been observed in cells exposed to a variety of metals, amino acids, ethanol and other conditions and treatments.

Another manifestation of the response is the development or acquisition of a thermotolerant phenotype. These phenotypes are developed by subjecting cells and cell masses such as tissues and organs to mild heat shock and then allowing them to recover at normal growth temperature. The thermotolerance thus acquired enables these cells to more effectively withstand a subsequent and more severe heat shock treatment which would otherwise do irreversible damage to the cells. Thermotolerant phenotypes also occur in cells exposed to other agents or treatments which elicit stress responses, such as heavy metals, arsenite, various amino acid analogs, and other metabolic poisons such as the sulfhydryl reducing agents iodoacetamide and p-chloromercuribenzoate. Thus, the stress response elicited by one particular agent or treatment can render the cells tolerant upon their exposure to a different agent or treatment which also can result in increased synthesis of one or more of the stress proteins. This is known as "cross-protection." A still further characteristic of thermotolerant phenotypes is "translational thermotolerance," which relates to both the rate of protein synthesis in general, the extent of protein synthesis, or both, by a cell after exposure to heat shock. In normal cells (those not yet made thermotolerant), protein synthesis rates drop upon exposure to heat shock and require considerable time to return to normal. In thermotolerant phenotypes, the recovery of protein synthesis is considerably faster.

Thermotolerance phenotypes have been induced in vivo in intact organisms and also in organs and tissues. Although the bulk of the experiments utilize hyperthermic treatments to induce thermotolerance, a growing body of data demonstrates that thermotolerance can be induced by treatment with certain chemical agents. For example, heat shock proteins have been induced in various cell cultures by treating them with agents such as sodium arsenite, cadmium chloride, cycloheximide, steroids, ethanol and nitric oxide.

Chemical agents have been used to induce the synthesis of heat shock proteins and for converting organisms and organs to a thermotolerant phenotype. For example, the insect hormone α-ecdysterone, induces thermotolerance and the synthesis of heat shock proteins in Drosophila (Buzin et al., "The induction of a subset of heat shock proteins by drugs that inhibit differentiation in Drosophila embryonic cell cultures;" In, HEAT SHOCK: FROM BACTERIA TO MAN, Schlesinger et al., Eds. Cold Spring Harbor, New York, pp. 387–394 (1982)). In Drosophila, an increased thermotolerance arises concomitant with the synthesis of heat shock proteins (Berger et al., Small heat shock proteins in Drosophila may confer thermal tolerance, *Exp. Cell. Res.* 147:437–442 (1983)). In rats, heat shock protein synthesis and thermotolerance have been induced by treating the experimental animals with sodium arsenite. Sodium arsenite induced heat shock synthesis in the rats, particularly in the lungs. The heat shock protein (hsp 72) was detected as early as 2 hours following arsenite injection. The expression of heat shock proteins correlated with significant protection against cecal ligation and perforation induced mortality (Ribeiro et al., "Sodium arsenite induces heat shock protein-72 kilodalton expression in the lungs and protects rats against sepsis," *Critical Care Medicine* 22:922–929 (1994)).

While it is logical to speculate that the increased expression of the stress proteins is in some way related to the acquisition of thermotolerance, the actual basis by which the tolerant phenotype is manifested is still unclear. For example, the proteins whose rate of expression is increased by heat shock range widely in molecular weight, some being in the 20,000 dalton range and others ranging as high as 110,000 daltons, and the same proteins are not always increased at the same rates in all species. In addition to the stress proteins, thermotolerance is accompanied by other physiological changes which result from the initial priming stress treatment. These include activation of protein kinase/phosphatase cascades, rearrangements of the cytoskeleton, membrane fluidity changes, changes in intracellular ions, and changes in cell growth and cell cycle. The type of contribution made by the stress proteins and the degree and manner in which these proteins interact with these other physiological changes raise many questions about the mechanism by which thermotolerance is actually achieved. Although there is broad correlation in the literature between heat shock protein synthesis and the induction of thermotolerance, in view of the multitude of factors involved, one cannot definitively conclude that an observed increase in the expression of certain stress proteins is a clear indication that thermotolerance will follow.

Further background information relevant to this invention is found in reports on the class of antibiotics known as benzoquinonoid ansamycins. These include the herbimycins A, B and C, geldanamycin, and various derivatives and analogs of these compounds. These compounds are known to exhibit antitumor activity and, in the case of the herbimycins, herbicidal, antiviral and anti-angiogenic activity as well. Explorations of the antitumor activity of these compounds have shown that these compounds inhibit p60$^{v-}$ src, a tyrosine-specific protein kinase, and thereby reverse the transformation of Rous sarcoma virus-transformed cells, possibly by binding to the kinase. More recent studies have suggested that these compounds can bind to hsp90. Whiteseil, L., et al., "Inhibition of heat shock protein HSP90-pp60$^{v-src}$ heteroprotein complex formation by benzoquinone ansamycins: Essential role for stress proteins in oncogenic transformation," *Proc. Natl. Acad. Sci. USA* 91:8324–8328 (1994). Because hsp90 is known to be important for the maturation of p60$^{v-src}$, reversion of the transformed phenotype may be due to the inability of the cells in the presence of the benzoquinonoid ansamycins to properly produce active and mature p60$^{v-src}$.

In the course of these explorations, it was discovered that herbimycin A induced the synthesis of a 70-kDa protein in A431 human epidermoid carcinoma cells, and that this protein is one of the heat stress proteins referred to above. Murakami, Y., et al., "Induction of hsp 72/73 by herbimycin A, an inhibitor of transformation by tyrosine kinase oncogenes," *Experimental Cell Research* 195:338–344 (1991). In their conclusions from these findings, however, Murakami, et al. acknowledged that although the heat shock proteins are thought to play a role in certain cellular processes, the exact function of heat shock proteins remains obscure. It is significant to note that Murakami, et al. speculate that herbimycin A may associate with newly synthesized proteins, in particular the EGF receptors, and thereby inhibit proper maturation of the receptors. In addition, they suggested that this interference with EGF receptor maturation might lead to increased hsp70 synthesis. Murakami, et al. refrain from any reference to thermotolerance, or from speculating as to whether herbimycin A itself can create thermotolerance, aside from its ability to induce the one stress protein that the authors observed. Murakami, et al. also suggested that other proteins (60- and 90-kilodalton) were increased as a result of herbimycin A exposure, but the authors did not prove that these proteins were heat shock proteins.

Accordingly, given the knowledge of the complexity of the heat shock response, there is no suggestion in the literature that thermotolerance can be induced by any means other than agents or treatments which lead to the general accumulation of abnormally folded proteins.

SUMMARY OF THE INVENTION

It has now been discovered that thermotolerance is induced in living cells and cell masses such as tissues, organs and whole organisms by the administration of benzoquinonoid ansamycins. The unusual nature of this discovery is that while the administration of these compounds also results in an increase in the expression of heat stress proteins, this increase is not accompanied by many of the other physiological changes which have been observed when the stress response is induced by heat shock or by known stress inducers such as L-azetidine-2-carboxylic acid (azc). Included among these physiological changes associated with the stress response are an interference with the folding of proteins immediately following their synthesis, the partial denaturation and aggregation of mature intracellular proteins, the redistribution of the intermediate filament cytoskeleton of the cell, causing the filaments to localize in and around the nucleus, and a prolonged period subsequent to heat shock in which protein synthesis is temporarily suspended. In accordance with this invention, benzoquinonoid ansamycins are observed to elicit thermotolerance without causing these changes or any other apparent adverse effects on cells. The ansamycins in fact offer an advantage over heat shock induction of the stress proteins by continuing to increase the expression and accumulation of the stress proteins as long as the drug is present. This is in contrast to classical stressors, where the continued expression is dependent on both the severity of the stress and the relative preexisting levels of the various stress proteins.

The discovery that thermotolerance, as opposed to merely an increase in the synthesis of heat shock proteins, is inducible by pharmacological means has major implications for the preservation, treatment and handling of cells and cellular materials, both in vivo and in vitro. Ischemia and reperfusion injury in various animal organs and tissues are known to result in an induction of the stress response. The induction of the heat shock proteins during ischemic injury is thought to be due to the resultant diminishment in intracellular levels of ATP. Subsequent reperfusion is thought to cause further injury via the production of oxygen radicals. Both of these insults (ATP depletion and oxygen radicals) interfere with normal protein folding and/or maturation and therefore lead to the accumulation of abnormally folded proteins.

Accordingly, the risks accompanying these aforementioned injuries can be reduced or eliminated by prior treatment with the agents disclosed herein, in a manner analogous to the protection provided by a prior sublethal heat shock treatment. Thermotolerant phenotypes developed in accordance with this invention will thus have increased protection against heart attack and stroke, and other types of incidents, injuries or surgical procedures in which blood flow to a particular organ or tissue is reduced or interrupted. Tissue and organ transplantations will also benefit from the increased protection afforded by the acquisition of thermotolerance according to this invention. Excised tissues and organs made thermotolerant prior to excision will survive for longer periods of time while awaiting implant, and once implanted, they will recover normal functioning faster.

These and other features and advantages of the invention will be more evident from the description which follows.

DETAILED DESCRIPTION OF THE INVENTION AND PREFERRED EMBODIMENTS

Figure 1:
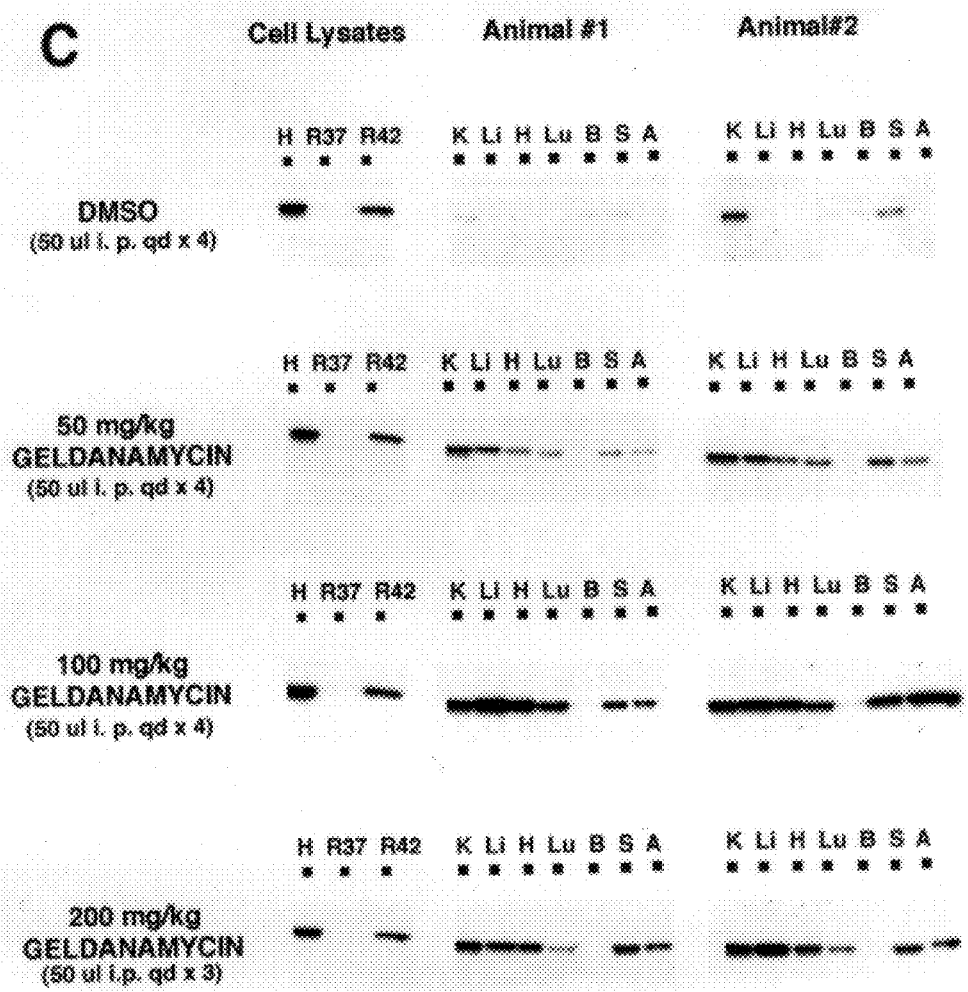
FIG. 1 displays the Western Blot Analysis data from two mice to which the benzoquinonoid ansamycin, geldanamycin was administered

Benzoquinonoid ansamycins suitable for use in the present invention include those of the following formula, with ring vertices as shown:

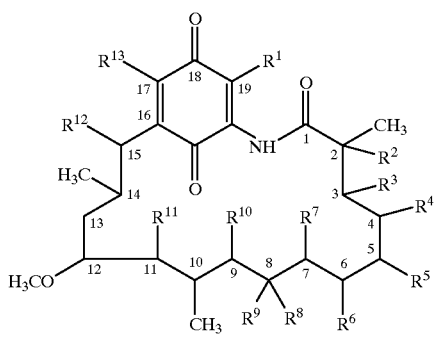

in which:

$R^1$ is H, halogen, OH, or $OCH_3$;

$R^2$ and $R^3$ are either both H or together form a double bond between ring vertices 2 and 3;

$R^4$ and $R^5$ are either both H or together form a double bond between ring vertices 4 and 5;

$R^6$ is H, halogen, OH, $CH_3$, or $OCH_3$;

$R^7$ either is $NH_2COO$ or is combined with $R^{10}$ to form NHCOO bridging ring vertices 7 and 9;

$R^8$ is H or $CH_3$;

$R^9$ either is OH or is combined with $R^{10}$ to form either (a) a double bond between ring vertices 8 and 9 or (c) a single oxy oxygen (—O—) bridging ring vertices 8 and 9;

$R^{10}$ is combined with either $R^7$ or $R^9$ in accordance with the definitions of $R^7$ and $R^9$;

$R^{11}$ is H, OH, $CH_3$, or $OCH_3$;

$R^{12}$ is H, OH, $CH_3$, or $OCH_3$; and $R^{13}$ is H, halogen, OH, or $OCH_3$.

Within this genus of compounds, certain subgenera are preferred. For example, the halogen atoms are preferably chlorine (Cl) or bromine (Br); $R^1$ is preferably H, Cl or Br; $R^6$ is preferably $OCH_3$, Cl or Br; $R^{11}$ is preferably OH or $OCH_3$; $R^{12}$ is preferably H, OH or $OCH_3$; and $R^{13}$ is preferably H or $OCH_3$. Further preferred subgenera are those with double bonds between ring vertices 2 and 3, 4 and 5, and 8 and 9.

Examples of known benzoquinonoid ansamycins within the formula are shown in Table 1, below, in which the compounds are defined by the R-groups used in the formula.

be isolated from natural sources, or synthesized by simple chemical modification of the naturally occurring substances. The herbimycins, for example, can be isolated from the fermentation broth of *Streptomyces hygroscopus* AM-3672. The 8,9-epoxy derivative of herbimycin A can be obtained by treatment of herbimycin A with m-chloroperbenzoic acid. The 8,9-epoxy derivative can then be treated with boron trifluoride etherate to obtain the 7,9-cyclic carbamate derivative. The 19-bromo derivative can be obtained from herbimycin A by treatment with pyridinium hydrobromide perbromide. The 6-chloro-6-demethoxy derivative can be obtained by treating herbimycin A with boron trichloride, and the 2,3,4,5-tetrahydro derivative can be obtained from herbimycin A by catalytic hydrogenation. Geldanamycin can be isolated from the filtered beer of *Streptomyces hygroscopus* var. *geldanus* var. *nova*. Macbecin I can be isolated from the fermentation broth of Nocardia sp. C-14919.

This invention is applicable to the treatment of both individual cells and cell aggregates such as tissues, organs, and whole body organisms, and will be effective upon administration either in vitro or in vivo. Examples of types of cells within the contemplation of this invention are blood cells, tissue cells, and reproductive cells, and particularly commercially available cell lines such as hybridomas. Other specific examples are oocytes, leukocytes, erythrocytes, platelets, pancreatic islets and hepatocytes. Examples of tissues are connective tissue, muscle tissue, nervous tissue, and epidermal tissue. Examples of organs are liver, spleen, kidney, heart, brain, lung, pancreas, ovary and stomach. Whole body organisms include embryos as well as mature animals and humans. The invention is of primary interest for mammalian cells, tissues and organs, including those of humans, domesticated animals, and livestock.

As mentioned above, it is known that tolerance induced by one type of stressor (heat, for example) is effective against subsequent exposure to other types of stressors (chemical agents, for example, or vice versa). The tolerance induced by the present invention is thus a generalized stress tolerance, and is useful in protecting cells, tissues, and organs in a variety of situations where stress injuries or loss of viability can occur. The invention is thus useful, for example as a treatment for patients, whether human or animal, prior to surgery by lowering the risks associated with surgery, such as physical trauma and adverse respiratory and coronary reactions. For effective results, the benzoquinonoid ansamycin is administered sufficiently in advance of the surgery to allow the tolerance to fully develop. Treatment is therefore administered at least about

|  | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | $R^{13}$ |
|---|---|---|---|---|---|---|---|---|---|---|---|---|---|
| herbimycin A | H | double bond | double bond | | | $OCH_3$ | $NH_2COO$ | $CH_3$ | double bond | | $OCH_3$ | $OCH_3$ | H |
| herbimycin B | H | double bond | double bond | | | $OCH_3$ | $NH_2COO$ | $CH_3$ | double bond | | OH | $OCH_3$ | H |
| herbimycin C | H | double bond | double bond | | | $OCH_3$ | $NH_2COO$ | $CH_3$ | double bond | | OH | OH | H |
| 8,9-epoxy-HA* | H | double bond | double bond | | | $OCH_3$ | $NH_2COO$ | $CH_3$ | —O— | | $OCH_3$ | $OCH_3$ | H |
| HA-7,9-cyclic carbamate | H | double bond | double bond | | | $OCH_3$ | with $R^{10}$: —NHCOO— | $CH_3$ | OH | see $R^7$ | $OCH_3$ | $OCH_3$ | H |
| 19-bromo-HA | Br | double bond | double bond | | | $OCH_3$ | $NH_2COO$ | $CH_3$ | double bond | | $OCH_3$ | $OCH_3$ | H |
| 6-chloro-6-demethoxy-HA | H | double bond | double bond | | | Cl | $NH_2COO$ | $CH_3$ | double bond | | $OCH_3$ | $OCH_3$ | H |
| 2,3,4,5-tetrahydro-HA | H | H | H | H | H | $OCH_3$ | $NH_2COO$ | $CH_3$ | double bond | | $OCH_3$ | $OCH_3$ | H |
| geldanamycin | H | double bond | double bond | | | $OCH_3$ | $NH_2COO$ | $CH_3$ | double bond | | OH | H | $OCH_3$ |
| macbecin I | H | double bond | double bond | | | $OCH_3$ | $NH_2COO$ | $CH_3$ | double bond | | $OCH_3$ | $OCH_3$ | H |

*"HA": herbimycin A

Benzoquinonoid ansamycins are known compounds which are obtainable from commercial drug suppliers, or can eight hours prior to the surgery, and preferably from about eight hours to about 24 hours, or the day before surgery. As a further example, this invention is also useful as a treatment for organs excised from organ donors for transplantation. Treatment of such organs in accordance with this invention will prolong the shelf life or viability of the excised organs while they are being transported to the patients awaiting them. A further use of this invention is in the treatment of tissue-cultured organs and cells, where incorporation of the benzoquinonoid ansamycins in the culture medium will enhance the viability of the organs or cells.

In the practice of this invention, the benzoquinonoid ansamycins can be administered in vivo by either parenteral, peritoneal, topical, oral, or local (such as aerosol or transdermal) methods of administration. The compounds can be administered in a variety of unit dosage forms depending upon the method of administration. For example, unit dosage forms suitable for oral administration include powder, tablets, pills, capsules and lozenges. Parenteral administration can be achieved by intravenous means or by administration into a body cavity or lumen of an organ.

The formulations for administration will commonly comprise a solution or emulsion of the compound in a pharmaceutically acceptable, preferably aqueous, carrier. For those compounds which are not water-soluble, the compounds can be derivatized in known manners to achieve water solubility. Buffered saline or any of physiologically compatible aqueous carrier can be used. Otherwise, organic solvents such as dimethyl sulfoxide can be used. The concentration of the active compound in these formulations can vary widely, and will be selected primarily based on fluid volumes, viscosities, body weight and the like in accordance with the particular mode of administration selected, and the needs of the patient when administered to in vivo.

Typical dosages for intravenous administration are about 0.01 to about 100 mg per patient, preferably about 0.1 to about 10 mg. These levels are all considerably lower than the $LD_{50}$ for benzoquinonoid ansamycins (19 mg/kg in mice, as reported by GIBCO BRL, Life Technologies, Inc., Gaithersburg, Md., USA, commercial supplier of herbimycin A). Higher dosages may be used when the drug is administered to a site other than the blood stream, such as a body cavity or the lumen of an organ. Typical dosages for intraperitoneal administration are about 10 mg/kg to about 500 mg/kg, preferably about 50 mg/kg to about 200 mg/kg. Formulations for parenteral administration are known to those skilled in the art, and examples are described in *Remington's Pharmaceutical Science,* 15th ed., Mack Publishing Company, Easton, Pa., USA (1980). Independent of the route of administration, the doses can be administered once or more than once.

In vitro administration is readily performed by any of the various conventional methods. Cells growing in culture, for example, can be treated by including the compound in the culture medium at any of a wide range of concentrations, followed by removal of the cells from contact with the compound and permitting the thermotolerant phenotype a period of time to develop. Preferred concentrations range from about 0.01 to about 100 µg/mL, preferably about 0.1 to about 2.0 µg/mL. Typical development times for the acquisition of the tolerant phenotype range from about 8 hours to about 24 hours after administration of the drug.

The amounts of the benzoquinonoid ansamycins referred to herein as "effective amounts" are those amounts which will result in the induction of the synthesis of heat shock proteins and preferably, the acquisition of a thermotolerant phenotype. These amounts may vary depending on whether treatment is being administered to cells, tissues, organs or organisms, and on the method of administration. As a general, non-limiting guideline, an effective amount will generally be the same as the amounts administered in the prior art for the use of these compounds as antibiotics.

The following examples are offered for purposes of illustration, and are not intended to limit the invention in any manner.

EXAMPLES

Materials and General Methods

The antibiotic herbimycin A was purchased from GIBCO BRL, Life Technologies, Inc., Gaithersburg, Md., USA, and was prepared as a 500 µg/mL solution in dimethylsulfoxide. L-Azetidine-2-carboxylic acid (azc), actinomycin D, cycloheximide and apyrase were purchased from Sigma Chemical Company, St. Louis, Mo., USA. Antibodies to hsp73 (IB5), to GRP94 (9G10), to hsp28 (rabbit polyclonal specific for rodent form), and to hsp72 (C92) were purchased from StressGen Biotechnologies Corporation, Victoria, BC, Canada. The antibody to vimentin was purchased from Sigma Chemical Company. Rabbit polyclonal anti-hsp73 antibody used for the immunoprecipitation and Western blot studies was the same as that described by Brown, C. R., et al., "The constitutive and stress inducible forms of hsp70 exhibit functional similarities and interact with one another in an ATP-dependent fashion," *J. Cell Biology* 120:1101–1112 (1993). Antibody to the heat shock transcription factor was the same as that described by Baler, R., et al., "Activation of human heat shock genes is accompanied by oligomerization, modification, and rapid translocation of heat shock transcription factor HSF1," *Molecular Cell Biology* 13:2486–2496 (1993). [35S]-Methionine/[35S]-cysteine ("translabel," specific activity 1,120 Ci/mMol) was purchased from ICN Pharmaceuticals, Inc., Costa Mesa, Calif., USA.

Rat embryo fibroblasts (REF-52), mouse fibroblasts (NIH 3T3), human HeLa cells, and monkey-derived COS cells were grown at 37° C. in Dulbecco's Modified Eagle Medium (DMEM) supplemented with 10% fetal calf serum. Metabolic labeling (for periods of less than 6 hours) involved removal of the medium, washing of the cells in methionine-free DMEM, and subsequent incubation of the cells in methionine-free DMEM containing translabel. For long-term labeling of cells (greater than 6 hours), methionine-free DMEM (95%) plus complete DMEM (5%) supplemented with 5% calf serum and containing translabel was used. Following labeling, the cells were harvested by removal of the culture medium, washed with phosphate-buffered saline (PBS), and Laemmli sample buffer (LSB) was added. All lysates were immediately heated to 95° C. for 5 minutes and clarified at 14,000×g for ten minutes before subsequent processing.

Experiment 1. Confirmation of the Prior Art—Increase in Synthesis of Stress Proteins in Cells Subjected to Heat Shock and in Cells Treated with Herbimycin A It is noted from the prior art that both rodent cells and primate cells express at least the hsp72 and hsp73 proteins which reside in the cytoplasm and nucleus. In rodent cells, hsp73 is expressed constitutively in cells while hsp72 is expressed exclusively under conditions of metabolic stress. In primate cells, both of these proteins are expressed constitutively in cells, and stress causes a significant increase in hsp72 and a modest increase in hsp73. The following experiment confirms these known facts.

The cells used in this example were rat embryo fibroblasts (REF-52), NIH 3T3 mouse fibroblasts, human HeLa cells, and monkey-derived COS cells. The cells, growing at 37°

C., were divided into three groups, the first left untreated for use as a control, the second subjected to a 43° C. heat shock treatment for 90 minutes, and the third exposed to 1 μg/mL of herbimycin A for 2 hours. Following treatment, the culture medium was removed and the cells were extensively washed with fresh medium and labeled for three hours at 37° C. with 50 μCi/mL of [35S]methionine. The cells were harvested by solubilization in LSB and labeled proteins were analyzed by two-dimensional gel electrophoresis. Within each cell type, an equal amount of trichloroacetic acid (TCA) precipitable material (cpm) was applied to the gel, and fluorographs of the gels were taken.

Comparing the heat shock-treated cells with the untreated cells for the two rodent cell lines, REF-52 and NIH 3T3, the fluorographs revealed that in both cases the heat shock treatment produced either a new appearance or a several-fold increase in the sizes of the two bands representing hsp73 and hsp72, respectively, as well as a lesser but still noticeable increase in hsp90, and finally, increases in hsp28. In neither case was an obvious increase seen in two other stress proteins, GRP94 and GRP78.

Comparing the herbimycin A-treated cells with the untreated cells for these two cell lines, the fluorographs revealed increased expression of not only hsp28, hsp73 and hsp90, but also GRP78 and GRP94, an effect which had not been observed in the heat shock-treated cells. The protein hsp72 did not appear, however.

A similar comparison for the two primate cell lines revealed that each cell line exhibited a several-fold increase in the expression of hsp28, hsp72, hsp73, and hsp90 and a modest increase in the expression of GRP94 AND GRP78, all as a result of the heat shock treatment. Herbimycin A treatment resulted in a significant increase in expression of all of the major stress proteins, including hsp72. Increases in hsp28 synthesis were also observed in both the heat shock and herbimycin A treatments.

These tests not only confirm but extend the results reported by Murakami, Y., et al., "Induction of hsp 72/73 by herbimycin A, an inhibitor of transformation by tyrosine kinase oncogenes," *Exp. Cell Res.* 195:338–344 (1991). Not only hsp70 as reported by Murakami, et al., but all of the other constitutively expressed stress proteins were up-regulated by herbimycin A treatment.

Experiment 2. Further Studies of Herbimycin A-Induced Synthesis of Stress Proteins: Synthesis Rates vs. Time The cells used in this experiment were rat embryo fibroblasts (REF-52), treated by placement in a culture medium containing 1 μg/mL of herbimycin A for two hours. Following the treatment period, the culture medium was removed, the cells extensively washed with fresh (herbimycin-free) culture medium, and the cells further incubated at 37° C.

At various times following removal of the herbimycin A, the cells were metabolically labeled with [35S]methionine for one-hour periods. Control cells not treated with the drug were labeled in the same manner. The relative rate of synthesis of hsp73 was determined by harvesting the cells in LSB and performing immunoprecipitation using an anti-hsp73 antibody, using an equal number of cells from each sample, the immunoprecipitates analyzed by sodium dodecyl sulfate polyacrylamide gel electrophoresis (SDS-PAGE).

The immunoprecipitates indicated that even four hours following the cessation of exposure of the cells to the drug, the cells were still synthesizing hsp73 at rates substantially higher than that observed in the untreated cells. It was not until about 12 hours after cessation of exposure to the drug that the cells began to reduce their rate of hsp73 synthesis, and by 21 hours, the cells were expressing hsp73 at rates similar to those of the untreated cells.

To determine whether continuous exposure of the cells to the drug would result in a sustained increase in the rate of synthesis of the stress proteins, the labeling and detection procedure described above was repeated at various times during a sustained exposure of sixteen hours. The same cells were used, using herbimycin A at 1 μg/mL. The fluorographs indicated that even after sixteen hours of continuous exposure to herbimycin A, the cells were still synthesizing hsp73 at levels higher than the levels observed in the untreated cells.

Finally, an experiment was run to determine whether the herbimycin A-induced increase in the synthesis rate of stress protein resulted in an accumulation of the proteins. The cells were exposed for two hours at 37° C., as before, but this was followed by a twelve-hour recovery period in the absence of the drug. After the recovery period, the cells were harvested, the total protein was determined and an equal amount of total protein applied to gels for analysis by Western blotting. Following the Western blotting, the relative amounts of protein were quantitated by densitometry and plotted as percent increase or decrease relative to untreated controls. The plots showed that there were consistent increases in the overall amounts of hsp73 (approximately 20%), hsp28 (100%) and GRP94 (approximately 40%). Although not quantitated, it was also found that GRP78 and GRP75 (mitochondrial hsp70) also accumulated to higher levels. A similar test on heat shock-treated cells showed the same degree of increase in hsp73 and hsp28, an increase in hsp72, and a decrease in GRP94. These increases in the overall amounts of the stress proteins can vary somewhat depending on the particular cell type as well as the duration of exposure to the drug.

Experiment 3. Development of a Thermotolerant Phenotype

This experiment illustrates the ability of herbimycin A to develop a thermotolerant phenotype and compares the phenotype with that developed by heat shock treatment.

A group of REF-52 cells growing at 37° C. was exposed to a 43° C. heat shock treatment for ninety minutes, while a second group was treated with 1 μg/mL of herbimycin A for two hours, and a third group received no treatment at all. The heat shock-treated cells were returned to 37° C. after the heat shock treatment and the culture medium removed and replaced with fresh medium. For the herbimycin A treated cells, the culture medium was removed after the treatment, and the cells were washed and then placed in fresh culture medium. All cells were then allowed to recover for eight hours to allow for the development of thermotolerance.

All cells were then challenged with a relatively severe 45° C. heat shock treatment lasting 45 minutes. Following this heat shock treatment, all three groups of cells were returned to 37° C. for two hours, then trypsinized and subsequently replated to determine their relative viability by a colony formation assay. The control cells exhibited a survival rate of 0.03%, the prior heat shock-treated cells a survival rate of 87%, and the herbimycin-treated cells a survival rate of 82%, indicating that the herbimycin-treated cells acquired a thermotolerant phenotype approximately equal to that observed for those cells which had received a prior heat shock treatment.

Essentially identical results were obtained when the test was repeated using HeLa cells.

Experiment 4. Acquisition of Translational Thermotolerance

This experiment illustrates the ability of cells treated with herbimycin A to develop translational thermotolerance, i.e., to shorten the length of time that protein synthesis is inhibited as a result of heat shock.

A group of REF-52 cells growing at 37° C. was exposed to a 43° C. heat shock treatment for ninety minutes, while a second group was treated with 1 μg/mL of herbimycin A for two hours, and a third (control) group received no treatment at all. Recovery procedures identical to those of Experiment 4 were followed. All three groups of cells were then subjected to a 45° C. heat shock treatment for thirty minutes, then returned to 37° C. At various times (1, 2 and 4 hours) after their return to 37° C., the cells were pulse-labeled with [35S]methionine for one hour and harvested in LSB. Lysates were then applied to a gel, and the labeled proteins resolved by SDS-PAGE.

The fluorographs indicated that the control cells did not fully recover their protein synthesis activities until four hours following the severe (45° C./30 min) heat shock treatment. Upon recovery of protein synthesis, an increase was observed in the rate of synthesis of hsp90, hsp73 and hsp72. In the cells first made thermotolerant by prior heat shock exposure, protein synthesis activities had fully recovered within two hours of the severe heat shock treatment. In the cells first made thermotolerant by treatment with herbimycin A, protein synthesis activities were also fully recovered within two hours of the severe heat shock treatment.

Experiments 4 and 5 together show that in terms of both cell viability and recovery of metabolic activity, herbimycin A exposure for as little as two hours followed by recovery in the absence of the drug converts the cells to a thermotolerant phenotype.

Experiment 5. Comparison of Specific Cellular Effects: Effect on Folding of Newly Synthesized Proteins This experiment shows a distinction between a cellular effect observed with the administration of a chemical agent which is a known inducer of the stress response and that observed with the administration of herbimycin A.

Previous studies (Beckmann, R. P., et al., "Interaction of hsp70 with newly synthesized proteins: Implications for protein folding and assembly," Science 248:850–854 (1990)) have shown that in the normal unstressed cell, hsp73 interacts in a transient fashion with newly synthesized proteins, and that once synthesis is complete and folding of the polypeptide commences, the hsp73 chaperone is released. In cells exposed to the known stress inducer L-azetidine-2-carboxylic acid (azc) (an amino acid analog of proline), hsp73 interacts with newly synthesized polypeptides here as well, but forms a stable complex with the polypeptides, preventing them from folding properly. Due to their inability to fold properly (because of incorporation of the analog), the newly synthesized proteins continue to appear non-native and therefore remain bound to the hsp73 chaperone. The purpose of this experiment was to determine whether herbimycin A likewise interferes with the folding of newly synthesized proteins.

In this experiment, one group of REF-52 cells growing at 37° C. was exposed to azc at 5 mM concentration for four hours, another exposed to herbimycin A at 1 μg/mL for four hours, and a third exposed to neither and serving as a control. All cells were then pulse labeled for twenty minutes at 37° C. with [35S]methionine and then immediately harvested. Parallel plates of cells were treated in the same manner except that the pulse labeling was followed by extensive washing with fresh culture medium, and the cells were then further incubated at 37° C. for a two-hour chase period in the absence of label. Both the pulsed and the pulsed-chased cells were then harvested in PBS containing 0.1% Triton X-100 supplemented with the ATP depleting enzyme apyrase (at a final concentration of 10 U/mL). The samples were then incubated for twenty minutes on ice, and the lysates were adjusted to radioimmune precipitation assay conditions (1% Triton, 1% sodium deoxycholate in PBS), then immunoprecipitated using either nonimmune or rabbit anti-hsp73 polyclonal antibody. The resulting immunoprecipitates were then analyzed by SDS-PAGE and the proteins visualized by fluorography.

The fluorographs showed that at the stage immediately following the twenty-minute pulse labeling, all three cases, i.e., those treated with herbimycin A, those treated with azc, and the control, exhibited a significant number of newly synthesized proteins coprecipitating with hsp73. Differences appeared at the stage following the two-hour chase period, however. While the number of proteins coprecipitating with hsp73 was significantly less in all three groups, the fluorographs indicated that the azc-treated cells had a significantly greater proportion of proteins coprecipitating with hsp73 than did the control cells, while the fluorographs for the herbimycin-treated cells and the control cells were similar.

Thus, herbimycin A was shown not to interfere with the folding of newly synthesized proteins, in contrast to azc, leading to the conclusion that herbimycin A follows a mode of action distinct from that of the stress protein inducer azc.

Experiment 6. Further Comparison of Cellular Effects: Effect on Solubility of Cell Proteins Previous studies (Beckmann, R. P., et al., "Examining the function and regulation of hsp70 in cells subjected to metabolic stress," J. Cell Biology 117:1137–1150 (1992)) have shown that in cells undergoing heat shock treatment, many mature (i.e., already synthesized) intracellular proteins are rendered insoluble in detergents, apparently due to their partial denaturation and aggregation. The purpose of this experiment was to determine whether treatment with herbimycin A produces the same result.

REF-52 cells at approximately 70% confluency growing at 37° C. were labeled with [35S]methionine for twelve hours. The label-containing culture medium was then removed and the cells were extensively washed with fresh culture medium, then incubated at 37° C. for four hours. One group of these cells was then subjected to a 45° C. heat shock treatment for thirty minutes, a second exposed to 1 μg/mL of herbimycin A for two hours at 37° C., and a third left unexposed to serve as a control. Following the treatments, the cells of the first two groups were washed and returned to normal growth conditions. At zero, 3 or 6 hours later, PBS containing 0.1% Triton X-100 was added to the cells, the monolayers harvested and the lysates centrifuged at 14,000×g for ten minutes in an Eppendorf centrifuge at 4° C. The supernatant was then removed and adjusted to 1×LSB by the addition of a suitable amount of 5×LSB. The proteins present in the 14,000×g pellet (i.e., the Triton-insoluble material) were then dissolved in 2×LSB. An equal amount of the Triton-insoluble material from each group of cells was applied to an SDS-PAGE gel and analyzed.

The fluorographs showed that the cells subjected to heat shock experienced a noticeable increase in the proteins over a wide range of molecular weight partitioning into the detergent-insoluble fraction, relative to the control. The cells treated with herbimycin A, by contrast, did not show any appreciable increase in detergent insoluble proteins, and produced a fluorograph essentially identical to that of the control. This is still further evidence that herbimycin A follows a mode of action distinct from that of other known agents or treatments which induce a stress response and a subsequent thermotolerant phenotype.

Experiment 7. Further Comparison of Cellular Effects: Rearrangement of Intermediate Filament Cytoskeleton It has also been reported that many of the agents and treatments which are known to induce the stress response also result in the rapid rearrangement of the intermediate filament cytoskeleton (Falkner, F. G., et al., "Two *Drosophila melanogaster* proteins related to intermediate filament proteins of vertebrate cells," *J. Cell Biol.* 91:175–183 (1981); Thomas, G. P., et al., "Molecular and cellular effects of heat shock and related treatments of mammalian tissue culture cells," *Cold Spring Harbor Symp. Quant. Biol.* 46:985–996 (1982); and Welch, W. J., et al., "Morphological study of the mammalian stress response: characterization of changes in cytoplasmic organelles, cytoskeleton, and nucleoli and appearance of intranuclear actin filaments and rat fibroblasts after heat shock treatment," *J. Cell Biol.* 101:1198–1211 (1985)). Normally distributed throughout the cytoplasm and extending to the plasma membrane in the unstressed cell, the vimentin-containing intermediate filaments redistribute in and around the nucleus following heat shock treatment. The present experiment was conducted to determine whether this was also a result of herbimycin A treatment.

One group of REF-52 cells growing at 37° C. on glass coverslips was subjected to a 43° C. heat shock treatment for ninety minutes, another was exposed to 1 μg/mL of herbimycin A for two hours, and a third was left untreated to serve as a control. Following treatment, the cells were fixed by immersion in absolute methanol at −20° C. for two minutes, then washed in PBS. The cells were then analyzed for their distribution of the vimentin-containing intermediate filament cytoskeleton by indirect immunofluorescence using primary and secondary antibodies diluted in PBS supplemented with 5 mg/mL bovine serum albumin.

The results showed that the filament network in the heat shock-exposed cells had changed considerably, localizing around the nucleus as opposed to being essentially uniformly distributed in the cytoplasm as in the control cells. The cells treated with herbimycin A, however, did not show redistribution, but instead exhibited the same distribution of the filament network as the control cells. Further analysis of the cells four hours after removal of the cells from exposure to herbimycin A again revealed no change in the filament network. This is still further evidence that herbimycin A follows a mode of action distinct from other known methods of inducing stress proteins and the thermotolerant phenotype.

Experiment 8. Comparison of Intracellular Distribution of hsp73

It is reported in the literature that shortly after heat shock treatment much of the existing hsp73, normally present within the cytoplasm and to a lesser extend the nucleus, rapidly accumulates inside the nucleus, concentrating within the nucleolus. Velazquez, J. M., et al., "HSP70: Nuclear concentration during environmental stress; cytoplasmic storage during recovery," *Cell* 36:655–663 (1984); Welch, W. J., et al., "Nuclear and nucleolar localization of the 72,000 dalton heat shock protein in heat shock mammalian cells," *J. Biol. Chem.* 259:4501–4510 (1982); Brown, C. R., et al., "The constitutive and stress inducible forms of hsp70 exhibit functional similarities and interact with one another in an ATP-dependent fashion," *J. Cell Bio.* 120:1101–1112 (1993). The nucleolar locale of the protein is thought to be due to the high levels of what appear to be heat denatured preribosomal particles which therefore would represent a collection of relatively unfolded target proteins for the hsp73 chaperone (Welch, W. J., et al., "Morphological study of the mammalian stress response: characterization of changes in cytoplasmic organelles, cytoskeleton, and nucleoli and appearance of intranuclear actin filaments and rat fibroblasts after heat shock treatment," *J. Cell Biol.* 101:1198–1211 (1985)). The purpose of this experiment was to determine whether herbimycin A treatment has the same effect.

One group of REF-52 cells growing at 37° C. on glass coverslips was subjected to a 43° C. heat shock treatment for ninety minutes, another was exposed to 1 μg/mL of herbimycin A for two hours, and a third was left untreated to serve as a control. Following treatment, the cells were fixed by immersion in absolute methanol at −20° C. for two minutes, then washed in PBS. The cells were then analyzed for their distribution of hsp73 by indirect immunofluorescence using primary and secondary antibodies diluted in PBS supplemented with 5 mg/mL bovine serum albumin. Both phase contrast micrographs and fluorescent micrographs were taken.

The micrographs of the control cells showed hsp73 present within the cytosol and to a lesser extent within the nucleus. The micrographs of the cells subjected to heat shock treatment showed that most of the hsp73 was redistributed to the nucleus. The micrographs of the cells treated with herbimycin A were similar to those of the control cells, with no apparent redistribution of the hsp73. Again, these results indicate that herbimycin A has a mode of action distinct from that of heat shock treatment or other agents which induce stress protein synthesis and the thermotolerant phenotype.

Experiment 9. Comparison of Acquired Thermotolerance

It is reported in the literature that the amounts of stress proteins synthesized after heat shock depends in part on the preexisting levels of the proteins in the cells prior to the shock. DiDominico, B. J., et al., "The heat shock response is self regulated at both the transcriptional and post-transcriptional levels," *Cell* 31:593–603 (1982); Mizzen, L. A., et al., "Characterization of the thermotolerant cell. I. Effects on protein synthesis activity and the regulation of heat shock protein 70 expression," *J. Cell Biol.* 106:1105–1116 (1982). The purpose of this experiment was to determine if this self regulation also occurred when the stress proteins were induced by herbimycin A.

One group of REF-52 cells at approximately 70% confluency growing at 37° C. was subjected to a 43° C. heat shock treatment for ninety minutes, and another was left untreated to serve as a control. Both groups were then labeled for 8 hours at 37° C. with 3[H]-leucine and the labeled proteins analyzed by SDS-PAGE. A third group was subjected to a 43° C. heat shock treatment for ninety minutes, then returned to 37° C. for 8 hours, then subjected to a second 43° C. heat shock treatment for ninety minutes, following which these cells were labeled with 3[H]-leucine for 8 hours at 37° C. and analyzed by SDS-PAGE.

Comparison among the three fluorographs showed increased levels of the stress proteins in the lysates from the single heat shock treatment, but considerably less of an increase in the levels of the proteins in the lysates from those cells subjected to a second heat shock treatment. This confirmed the effects reported in the literature.

In a second part of the experiment, one group of REF cells growing at 37° C. was exposed to 1 μg/mL of herbimycin A for two hours, while a second group was left untreated as a control. The herbimycin A was then removed and both groups were labeled for two hours with 3[H]-leucine at 37° C. and the labeled proteins analyzed by SDS-PAGE. A third group was treated with herbimycin A in the same manner as the first group, then the drug removed and the cells further incubated at 37° C. for eight hours. These cells were then subjected a second time to the same herbimycin A treatment, the drug removed, and the cells labeled with 3[H]-leucine for two hours at 37° C., followed by SDS-PAGE.

Comparison among the three fluorographs from this second part of the experiment showed that the lysates from the group treated twice with herbimycin A exhibited essentially the same level of increase in the stress proteins as the lysates from the group treated only once.

This demonstrates that the autoregulatory effect of the heat shock treatment is not exhibited when stress protein synthesis is induced by herbimycin A. In contrast to heat shock treatment, increased expression of the various stress proteins continues for as long as herbimycin A is present, and is independent of the preexisting levels of the stress proteins in the cells prior to administration of the drug.

Experiment 10. Induction of Synthesis of Stress Proteins in vivo by Treatment with Geldanamycin The in vivo induction of hsp 72 synthesis by geldanamycin was studied in mice. Geldanamycin was administered intraperitoneally (i.p.) in varying doses as a solution in DMSO. The dosages ranged from 50 mg/kg to 200 mg/kg. Dosages of 50 mg/kg and 100 mg/kg were administered once a day for four days. A dosage of 200 mg/kg was administered once a day for 3 days. Each administration utilized a 50 µL aliquot of the geldanamycin/DMSO solution. Control animals were injected intraperitoneally with 50 µL aliqouts of DMSO without geldanamycin. The injections were made once a day for 4 days. Following the last administration of geldanamycin, the animals were kept for 24 hours prior to sacrifice. After sacrifice, the kidney, liver, heart, lung, brain, skin and an artery were assayed for the presence of hsp 72.

In addition to the in vivo experiments, a series of experiments on various cell cultures were performed. For each of the in vivo experiment at a particular dosage, a cell culture experiment at that dosage was run in parallel. The cultured cells included HeLa and rat embryo fibroblasts. The rat embryo fibroblasts consisted of two groups of cells which differed in their incubation temperature. One group was maintained at 37° C. The second group was incubated at 42° C.

The assay for hsp 72 was performed using Western Blot Analysis. Briefly, following excision, the organs and tissues were homogenized and the protein in the homogenates was quantified using the Braford analysis. 50 µg of protein from each organ were loaded onto a gel. The hsp 72 was visualized using an antibody (C92) specific for the stress-inducible form of hsp 72 in conjunction with chemiluminescence. The results of the Western Blot Analysis are displayed in FIG. 1.

The animals which were treated with geldanamycin demonstrated a dramatic increase in the synthesis of hsp 72 in every organ except the brain. The synthesis of hsp appeared qualitatively dependent on the dose of geldanamycin which was administered. In contrast, one control animal demonstrated no appreciable synthesis of hsp 72 following the i.p. administration of a 50 µL aliquot of DMSO, while hsp synthesis was minimally induced by DMSO in the kidney and skin of the second control animal. Thus, this experiment conclusively demonstrates that benzoquinonoid ansamycins are useful for the in vivo induction of stress protein synthesis and hence, by extension, benzoquinonoid ansamycins can also induce thermotolerance in organisms, organs and tissues.

The foregoing is offered primarily for purposes of illustration. It will be readily apparent to those skilled in the art that the dosages, methods of administration, and other parameters of the system described herein may be further modified or substituted in various ways without departing from the spirit and scope of the invention.

We claim:

1. A method for converting living biological matter selected from mammals and mammalian organs to a thermotolerant phenotype, said method comprising treating said living biological matter with a compound having the following formula, with ring vertices as shown:

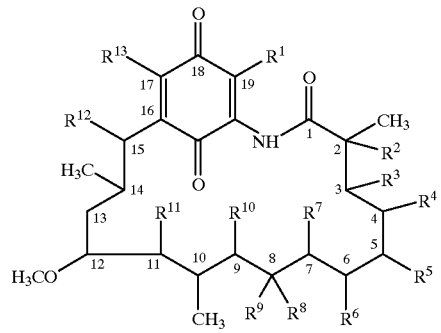

in which:
R$^1$ is a member selected from the group consisting of H, halogen, OH, and OCH$_3$;
R$^2$ and R$^3$ are either both H or together form a double bond between ring vertices 2 and 3;
R$^4$ and R$^5$ are either both H or together form a double bond between ring vertices 4 and 5;
R$^6$ is a member selected from the group consisting of H, halogen, OH, CH$_3$, and OCH$_3$;
R$^7$ either is NH$_2$COO or is combined with R$^{10}$ to form NHCOO bridging ring vertices 7 and 9;
R$^8$ is a member selected from the group consisting of H and CH$_3$;
R$^9$ either is OH or is combined with R$^{10}$ to form either (a) a double bond between ring vertices 8 and 9 or (c) a single oxy oxygen (—O—) bridging ring vertices 8 and 9;
R$^{10}$ is combined with either R$^7$ or R$^9$ in accordance with the definitions of R$^7$ and R$^9$;
R$^{11}$ is a member selected from the group consisting of H, OH, OCH$_3$ and CH$_3$;
R$^{12}$ is a member selected from the group consisting of H OH, OCH$_3$ and CH$_3$; and
R$^{13}$ is a member selected from the group consisting of H, halogen, OH, and OCH$_3$;
at a dosage of about 50 to about 200 mg/kg.

2. A method in accordance with claim 1 in which said compound is defined such that ring vertices 2 and 3 are joined by a double bond, and ring vertices 4 and 5 are joined by a double bond.

3. A method in accordance with claim 2 in which said compound is defined such that ring vertices 8 and 9 are joined by a double bond.

4. A method in accordance with claim 2 in which said compound is defined such that R$^1$ is a member selected from the group consisting of H, Cl and Br.

5. A method in accordance with claim 2 in which said compound is defined such that R$^6$ is a member selected from the group consisting of OCH$_3$, Cl and Br.

6. A method in accordance with claim 2 in which said compound is defined such that R$^{11}$ is a member selected from the group consisting of OH and OCH$_3$.

7. A method in accordance with claim 2 in which said compound is defined such that R$^{12}$ is a member selected from the group consisting of H, OCH$_3$ and OH.

8. A method in accordance with claim 2 in which said compound is defined such that R$^{13}$ is a member selected from the group consisting of H and OCH$_3$.

9. A method in accordance with claim 1 in which said compound is a member selected from the group consisting of herbimycin A, herbimycin B, herbimycin C, 8,9-epoxy-herbimycin A, herbimycin A-7,9-cyclic carbamate, 19-bromo-herbimycin A, 6-chloro-6-demethoxy-herbimycin A, 2,3,4,5-tetrahydroherbimycin A, geldanamycin, and macbecin I.

10. A method in accordance with claim 1 in which said compound is a member selected from the group consisting of herbimycin A, herbimycin B, herbimycin C, geldanamycin, and macbecin I.

11. A method in accordance with claim 1 in which said compound is herbimycin A.

12. A method in accordance with claim 1 in which said compound is administered to said living biological matter in a dosage of from about 10 mg/kg to about 500 mg/kg.

13. A method for inducing heat shock protein synthesis in an organism prior to undergoing a surgical procedure, said method comprising administering to said organism at least about 8 hours prior to said procedure a compound having the following formula, with ring vertices as shown:

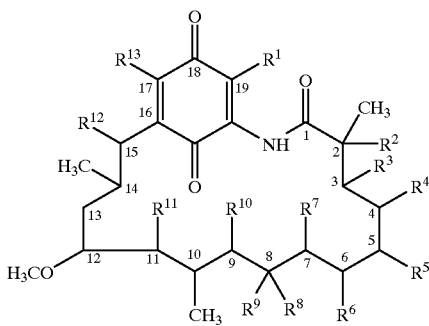

in which:
R$^1$ is a member selected from the group consisting of H, halogen, OH, and OCH$_3$;
R$^2$ and R$^3$ are either both H or together form a double bond between ring vertices 2 and 3;
R$^4$ and R$^5$ are either both H or together form a double bond between ring vertices 4 and 5;
R$^6$ is a member selected from the group consisting of H, halogen, OH, CH$_3$, and OCH$_3$;
R$^7$ either is NH$_2$COO or is combined with R$^{10}$ to form NHCOO bridging ring vertices 7 and 9;
R$^8$ is a member selected from the group consisting of H and CH$_3$;
R$^9$ either is OH or is combined with R$^{10}$ to form either (a) a double bond between ring vertices 8 and 9 or (c) a single oxy oxygen (—O—) bridging ring vertices 8 and 9;
R$^{10}$ is combined with either R$^7$ or R$^9$ in accordance with the definitions of R$^7$ and R$^9$;
R$^{11}$ is a member selected from the group consisting of H, OH, CH$_3$, and OCH$_3$;
R$^{12}$ is a member selected from the group consisting of H, OH, CH$_3$, and OCH$_3$; and
R$^{13}$ is a member selected from the group consisting of H, halogen, OH, and OCH$_3$
in an amount effective to induce said synthesis.

14. A method in accordance with claim 13 in which said compound is a member selected from the group consisting of herbimycin A, herbimycin B, herbimycin C, 8,9-epoxy-herbimycin A, herbimycin A-7,9-cyclic carbamate, 19-bromo-herbimycin A, 6-chloro-6-demethoxy-herbimycin A, 2,3,4,5-tetrahydroherbimycin A, geldanamycin, and macbecin I.

15. A method in accordance with claim 13 in which said compound is a member selected from the group consisting of herbimycin A, herbimycin B, herbimycin C, geldanamycin, and macbecin I.

16. A method in accordance with claim 13 in which said compound is herbimycin A.

17. A method for inducing heat shock protein synthesis in an organ prior to transplantation into a patient, said method comprising treating said organ with a compound having the following formula, with ring vertices as shown:

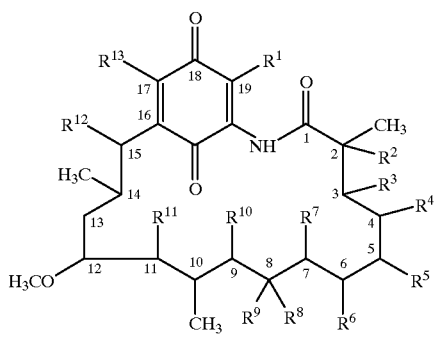

in which:
R$^1$ is a member selected from the group consisting of H, halogen, OH, and OCH$_3$;
R$^2$ and R$^3$ are either both H or together form a double bond between ring vertices 2 and 3;
R$^4$ and R$^5$ are either both H or together form a double bond between ring vertices 4 and 5;
R$^6$ is a member selected from the group consisting of H, halogen, OH, CH$_3$, and OCH$_3$;
R$^7$ either is NH$_2$COO or is combined with R$^{10}$ to form NHCOO bridging ring vertices 7 and 9;
R$^8$ is a member selected from the group consisting of H and CH$_3$;
R$^9$ either is OH or is combined with R$^{10}$ to form either (a) a double bond between ring vertices 8 and 9 or (c) a single oxy oxygen (—O—) bridging ring vertices 8 and 9;
R$^{10}$ is combined with either R$^7$ or R$^9$ in accordance with the definitions of R$^7$ and R$^9$;
R$^{11}$ is a member selected from the group consisting of H, OH, CH$_3$, and OCH$_3$;
R$^{12}$ is a member selected from the group consisting of H, OH, CH$_3$, and OCH$_3$; and
R$^{13}$ is a member selected from the group consisting of H, halogen, OH, and OCH$_3$
in an amount effective to induce said synthesis.

18. A method in accordance with claim 17 which said compound is a member selected from the group consisting of herbimycin A, herbimycin B, herbimycin C, 8,9-epoxy-herbimycin A, herbimycin A-7,9-cyclic carbamate, 19-bromo-herbimycin A, 6-chloro-6-demethoxy-herbimycin A, 2,3,4,5-tetrahydroherbimycin A, geldanamycin, and macbecin I.

19. A method in accordance with claim 17 in which said compound is a member selected from the group consisting of herbimycin A, herbimycin B, herbimycin C, geldanamycin, and macbecin I.

20. A method in accordance with claim 17 in which said compound is herbimycin A.

21. A method for inducing a thermotolerant phenotype in a mammal undergoing an ischemia/reperfusion insult, said method comprising administering to said mammal a compound having the following formula with ring vertices as shown:

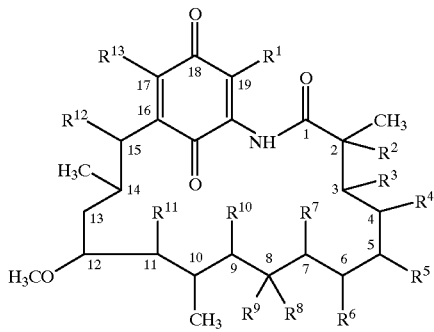

in which:
- $R^1$ is a member selected from the group consisting of H, halogen, OH, and $OCH_3$;
- $R^2$ and $R^3$ are either both H or together form a double bond between ring vertices 2 and 3;
- $R^4$ and $R^5$ are either both H or together form a double bond between ring vertices 4 and 5;
- $R^6$ is a member selected from the group consisting of H, halogen, OH, $CH_3$, and $OCH_3$;
- $R^7$ either is $NH_2COO$ or is combined with $R^{10}$ to form NHCOO bridging ring vertices 7 and 9;
- $R^8$ is a member selected from the group consisting of H and $CH_3$;
- $R^9$ either is OH or is combined with $R^{10}$ to form either (a) a double bond between ring vertices 8 and 9 or (c) a single oxy oxygen (—O—) bridging ring vertices 8 and 9;
- $R^{10}$ is combined with either $R^7$ or $R^9$ in accordance with the definitions of $R^7$ and $R^9$;
- $R^{11}$ is a member selected from the group consisting of H, OH, $CH_3$, and $OCH_3$;
- $R^{12}$ is a member selected from the group consisting of H, OH, $CH_3$, and $OCH_3$; and
- $R^{13}$ is a member selected from the group consisting of H, halogen, OH, and $OCH_3$;

in an amount effective in inducing such synthesis.

22. The method according to claim 21, wherein said administering occurs at a time prior to said insult occurring.

23. The method according to claim 21, wherein said insult is to a tissue that is a member selected from the group consisting of kidney, liver, heart, lung, skin, vasculature and combinations thereof.

24. The method according to claim 21, wherein said ischemia/reperfusion injury is caused by a member selected from the group consisting of stroke, myocardial infarction and transplantation.

* * * * *

UNITED STATES PATENT AND TRADEMARK OFFICE
CERTIFICATE OF CORRECTION

PATENT NO. : 6,015,659
DATED : January 18, 2000
INVENTOR(S) : Welch, et al.

It is certified that error appears in the above-indentified patent and that said Letters Patent is hereby corrected as shown below:

In column 18, line 57, after "claim 17" insert --in--.

Signed and Sealed this

Thirteenth Day of March, 2001

Attest:

NICHOLAS P. GODICI

Attesting Officer     Acting Director of the United States Patent and Trademark Office